United States Patent

Wijtsma et al.

[11] Patent Number: 6,005,254
[45] Date of Patent: Dec. 21, 1999

[54] IRRADIATION DEVICE

[75] Inventors: Jorrit Wijtsma; Boyd W. F. Mulder, both of Drachten, Netherlands

[73] Assignee: U.S. Philips Corporation, New York, N.Y.

[21] Appl. No.: 09/024,638

[22] Filed: Feb. 17, 1998

[30] Foreign Application Priority Data

Feb. 17, 1997 [EP] European Pat. Off. .............. 97200462

[51] Int. Cl.$^6$ .................................. A61N 5/06; G01J 1/00
[52] U.S. Cl. ..................................... 250/494.1; 250/493.1; 250/504 R
[58] Field of Search .............................. 250/494.1, 493.1, 250/504 R; 362/282, 287, 61

[56] References Cited

U.S. PATENT DOCUMENTS 4,866,284  9/1989  Frankena et al. ..................... 250/494.1

Primary Examiner—Edward P. Westin
Assistant Examiner—Nikita Wells
Attorney, Agent, or Firm—Ernestine C. Bartlett

[57] ABSTRACT

An irradiation device provided with a support which is hinged via an arm to a support and a housing which has a radiation emission plane and which comprises two units with radiation sources which are each hinged to the support about a respective axis transverse to the radiation emission plane and can be placed in certain positions relative to the support, said support comprising a third unit also provided with at least one radiation source between the pivot points of the two former units, which third unit is rotatable with resistance about an axis transverse to the radiation emission plane.

3 Claims, 3 Drawing Sheets

IRRADIATION DEVICE

BACKGROUND OF THE INVENTION

The invention relates to an irradiation device provided with a base which is hinged to a support and a housing by means of an arm, which housing has a radiation emission plane and comprises two units with radiation sources, each unit being connected to said support with hinging possibility about an axis transverse to the radiation emission plane and being placeable in certain positions relative to the support. Such an irradiation device is known from U.S. Pat. No. 4,866,284.

The known irradiation device is used for irradiating the human body with ultraviolet radiation. The housing is provided with units in which radiation sources, such as high-pressure lamps, with reflectors arranged behind them are accommodated. The radiation leaves the housing through the radiation emission plane (in front of which a filter may or may not have been placed). In the operational state of the device, the two units of the housing can be easily hinged away from one another by a user and placed in positions relative to the support such that irradiation of the body over a considerable length is possible. The device can be folded together into a compact unit and stored in a simple manner after use. It was found that the intensity of the suntanning effect was susceptible of improvement especially at the sides of the body when a person lying on a bed is irradiated with the known device.

SUMMARY OF THE INVENTION

It is an object of the invention to provide an irradiation device of the kind described in the opening paragraph with which an optimum irradiation result is obtained in the operational state at the sides of the body of a person under irradiation.

According to the invention, this object is achieved in that the support comprises a third unit also provided with at least one radiation source between the hinging points of the aforementioned two units, which third unit is rotatable with resistance relative to the support about an axis transverse to the radiation emission plane.

The device according to the invention renders possible not only a homogeneous irradiation of the body over substantially its entire length in the operational state, but in addition a user lying, for example, on a bed has the possibility of subjecting also the sides of parts of the body to a higher irradiance than with the known device owing to the presence of the third unit with one or several radiation sources.

In a preferred embodiment, the units of the housing are of elongate shape, while in the operational state two units can be placed in a position relative to the support in which their longitudinal axes lie in one another's extended direction, and the third unit can be placed in a position in which its longitudinal axis coincides substantially with the longitudinal axes of the other units and in a position in which its longitudinal axis is transverse to the longitudinal axes of the other units, as desired. The device is then easy to operate for a user, a homogeneous irradiation is obtained over the entire body, and especially the sides of the body are well irradiated in the operational state.

BRIEF DESCRIPTION OF THE DRAWINGS

Embodiments of the irradiation device according to the invention are shown in the drawing, in which.

BRIEF DESCRIPTION OF THE PREFERRED EMBODIMENTS

Figure 1:
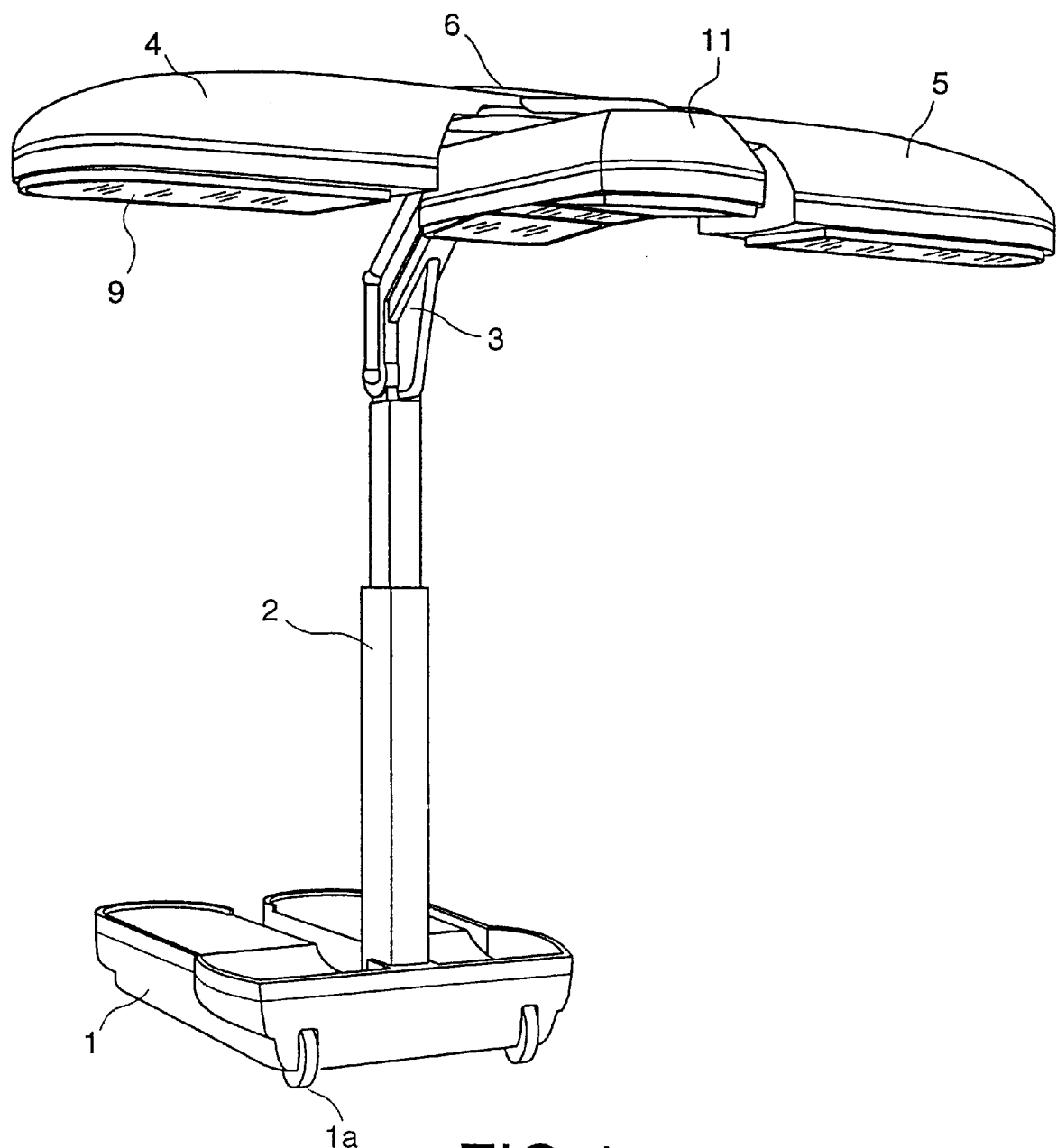
FIG. 1 is an elevation of the irradiation device according to the invention in an operational state.

The irradiation device of FIG. 1 comprises a base 1 which is provided with wheels 1a and which is connected to a support 6 and a housing by means of a telescopic arm 2 and an intermediate arm 3 connected thereto via hinges. This housing is composed of two elongate units 4 and 5 which can be hinged out until their longitudinal axes lie in one another's extended direction. A radiation source (such as a high-pressure mercury vapor discharge lamp in which also cobalt and iron are present in the discharge vessel) is arranged in each unit 4, 5, with a respective reflector placed behind it (see FIGS. 2 and 3). A radiation emission plane is formed at the side of the two units facing the support. A radiation filter 9 is mounted in that location. The units 4 and 5 are hinged to a support 6. The axes 7 and 8 of the hinges in the support 6 (see FIG. 2) are transverse to the radiation emission plane (the "horizontal plane"). The term "transverse" is here understood to mean perpendicular with a deviation of up to approximately 30° in specific embodiments. The two units 4 and 5 are of a somewhat elongate shape. As is shown in the embodiment, the units 4 and 5 are so positioned relative to the support 6 (for example by locking mechanisms) that the longitudinal axes of the two units lie in one line. Between the pivot points 7 and 8, the support 6 is provided with a third unit 11 which is also provided with a radiation source and which is rotatable with resistance in the support 6 about an axis 10 which also extends transversely to the radiation emission plane. This unit can be secured in a fixed position relative to the support by a user. The unit 11 is elongate in shape and comprises two radiation sources. The unit is locked in a position in which the longitudinal axis of the unit 11 is transverse to the longitudinal axes of the units 4 and 5 in this example. In the embodiment shown, a cross-shaped arrangement is thus obtained, as seen from above, with the housing composed of three units comprising four radiation sources.

Figure 3:
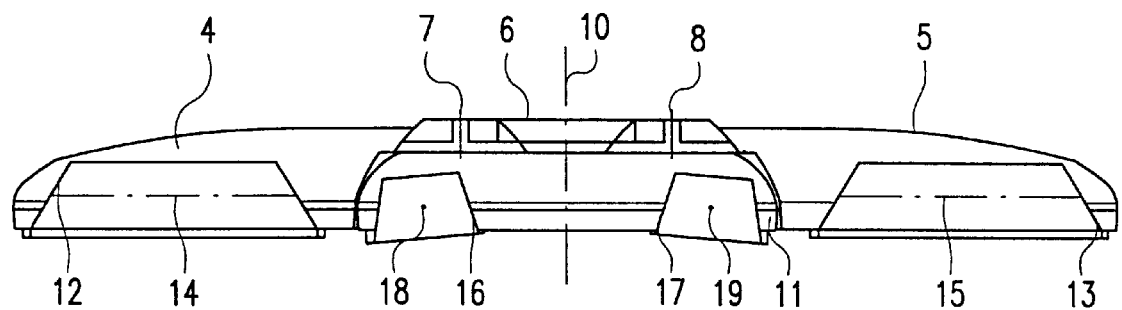
FIG. 3 is also a side elevation of the housing of the irradiation device according to the invention, a third unit being shown in the folded state.

In FIG. 3, the unit 11 is so locked relative to the units 4 and 5 that the longitudinal axes of the units substantially coincide.

Figure 2:
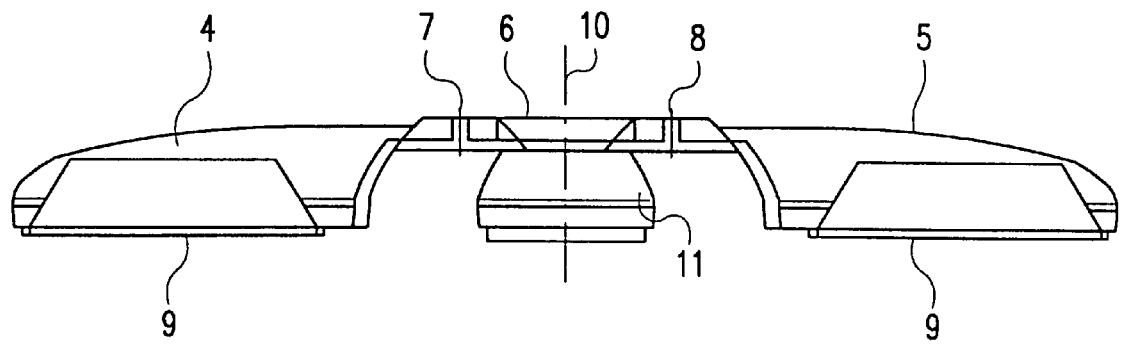
FIG. 2 is a side elevation of the housing.

A channel-shaped, faceted reflector is present behind each radiation source in the housing. These reflectors are referenced 12 and 13 for the units 4 and 5 in FIG. 3. The central axes 14 and 15 of these channel-shaped reflectors coincide with the longitudinal axes of the units 4 and 5. The channel-shaped reflectors 16, 17 in the unit 11 by contrast each have a central axis 18, 19 which is transverse to the longitudinal axis of the relevant unit. In a preferred position for the user as depicted in FIG. 2, the central axes of all reflectors point in the same direction, with the result that a homogeneous irradiation of the body is obtained.

Figure 4:
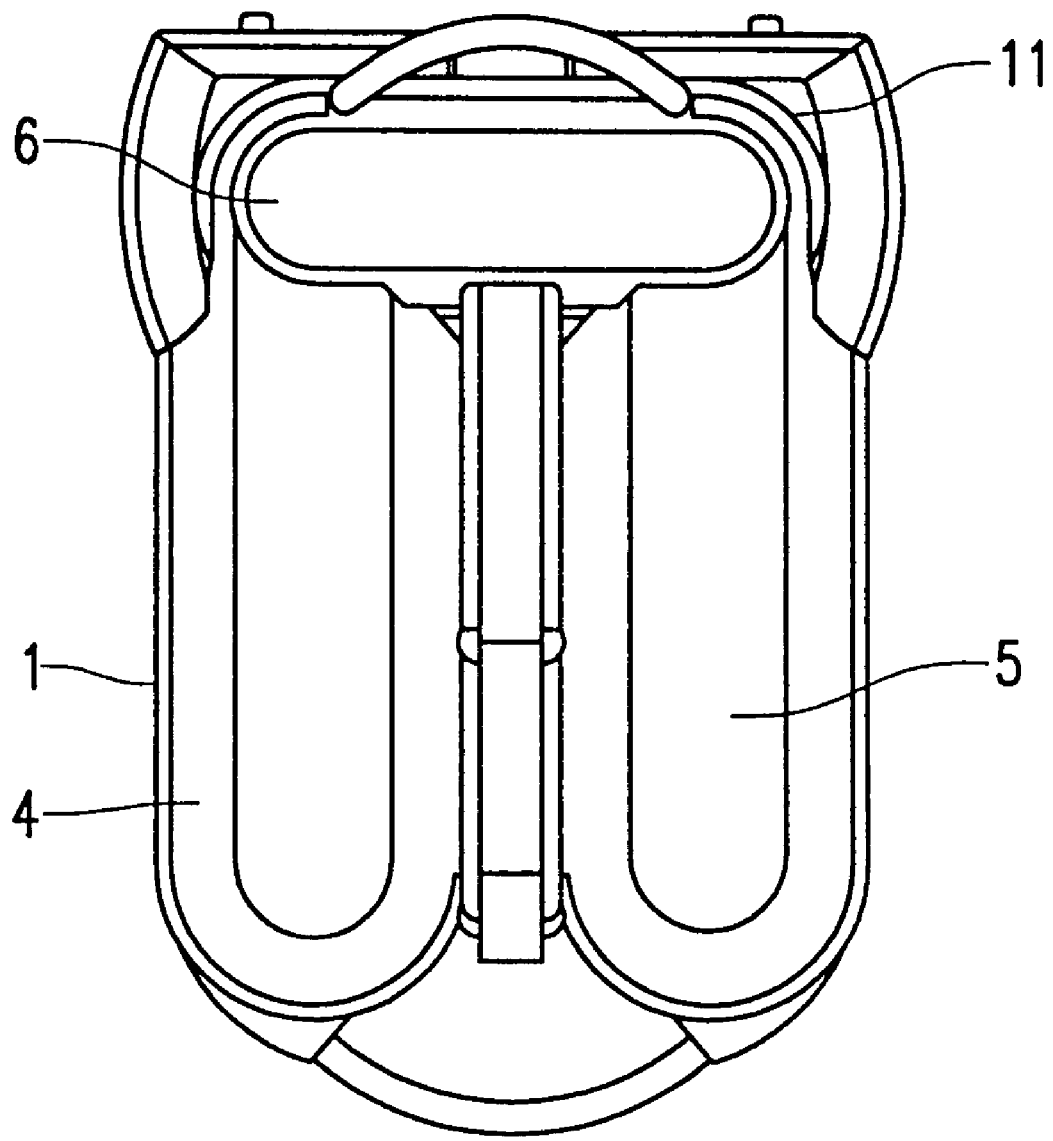
FIG. 4 diagrammatically shows the device in the fully folded state.

FIG. 4 shows the compact, folded-in state of the device. The device can then be stored. During folding-up, a user first folds the unit 11 into a position as shown in FIG. 3, whereupon the units 4 and 5 can be folded in by means of the hinges (about axes 7 and 8) through 90°. Then the entire assembly is received inside the base 1 via the arms 2 and 3.

High-pressure mercury vapor discharge lamps with a power rating of preferably between 400 W and 600 W are accommodated in the synthetic-resin units of the housing in the operational state of the device. The discharge vessel contains besides an operational quantity of mercury also a small quantity of cobalt and iron. Apart from infrared radiation, such lamps emit mainly UV-A radiation (315–400 nm) and UV-B radiation (280–315 nm). The UV-B radiation, however, is largely blocked out by the radiation filter 9.

We claim:

1. An irradiation device provided with a base which is hinged to a support and a housing by means of an arm, which housing has a radiation emission plane and comprises two units with radiation sources, each unit being connected to said support with hinging possibility about an axis transverse to the radiation emission plane and being placeable in certain positions relative to the support, wherein the support comprises a third unit also provided with at least one radiation source between the hinging points of the aforementioned two units, which third unit is rotatable with resistance relative to the support about an axis transverse to the radiation emission plane.

2. An irradiation device as claimed in claim 1, wherein the units of the housing are of elongate shape, while in the operational state two units can be placed in a position relative to the support in which their longitudinal axes lie in one another's extended direction, and the third unit can be placed in a position in which its longitudinal axis coincides substantially with the longitudinal axes of the other units and in a position in which its longitudinal axis is transverse to the longitudinal axes of the other units, as desired.

3. An irradiation device as claimed in claim 2, wherein a channel-shaped reflector is present behind each radiation source in the housing, the central axis in the first two units extending parallel to the longitudinal axis of said units, and the central axis of the channel-shaped reflector in the third unit extending transversely to the longitudinal axis of the third unit.

* * * * *